(12) United States Patent
Yamagata (10) Patent No.: US 10,481,103 B2
(45) Date of Patent: Nov. 19, 2019

(54) INSPECTION DEVICE, INSPECTION FACILITY AND INSPECTION DEVICE FAILURE CONFIRMATION METHOD

(71) Applicant: TOYOTA JIDOSHA KABUSHIKI KAISHA, Toyota-shi, Aichi-ken (JP)

(72) Inventor: Yoshihiro Yamagata, Toyota (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 16/157,625

(22) Filed: Oct. 11, 2018

(65) Prior Publication Data

US 2019/0120772 A1   Apr. 25, 2019

(30) Foreign Application Priority Data

Oct. 20, 2017   (JP) .................................. 2017-203906

(51) Int. Cl.
| | |
|---|---|
| *G01N 21/95* | (2006.01) |
| *G01N 21/84* | (2006.01) |
| *G02B 7/00* | (2006.01) |
| *H01M 8/04664* | (2016.01) |
| *G01N 21/88* | (2006.01) |
| *G01N 21/93* | (2006.01) |
| *G02B 27/28* | (2006.01) |

(52) U.S. Cl.
CPC .............. *G01N 21/95* (2013.01); *G01N 21/84* (2013.01); *G01N 21/8803* (2013.01); *G01N 21/93* (2013.01); *G02B 7/00* (2013.01); *H01M 8/04686* (2013.01); *G01N 2201/0683* (2013.01); *G02B 27/288* (2013.01)

(58) Field of Classification Search
CPC .... G01N 21/95; G01N 21/84; G01N 21/8803; G01N 21/93; G02B 7/00; H01M 8/04686
USPC ........................................................ 356/237.2
See application file for complete search history.

(56) References Cited

U.S. PATENT DOCUMENTS

| | | | |
|---|---|---|---|
| 9,377,395 B2 * | 6/2016 | Aharon | ................ A61B 5/0077 |
| 2005/0179891 A1 * | 8/2005 | Almogy | ............ G01N 21/9501 |
| | | | 356/237.2 |

FOREIGN PATENT DOCUMENTS

| | | |
|---|---|---|
| JP | 2012-002792 | 1/2012 |
| JP | 2014-188066 | 10/2014 |

* cited by examiner

*Primary Examiner* — Roy M Punnoose
(74) *Attorney, Agent, or Firm* — Finnegan, Henderson, Farabow, Garrett & Dunner, LLP (57) ABSTRACT

An inspection device is adapted for inspecting whether or not there is a foreign matter or dirt adhered to a surface of a workpiece or whether or not there is a scratch on the surface of the workpiece. A first polarizing plate having a polarizing axis in a first direction is attached to an open window of the cover part, and a second polarizing plate having a polarizing axis in a second direction orthogonal to the first direction is attached to the open window so as to open and close. In a state where the second polarizing plate is closed, the second polarizing plate overlaps the first polarizing plate. In a state where the second polarizing plate is open, the first polarizing plate and the second polarizing plate are present on a straight line connecting the outside light source and the fuel cell.

9 Claims, 6 Drawing Sheets

INSPECTION DEVICE, INSPECTION FACILITY AND INSPECTION DEVICE FAILURE CONFIRMATION METHOD

INCORPORATION BY REFERENCE

The disclosure of Japanese Patent Application No. 2017-203906 filed on Oct. 20, 2017 including the specification, drawings and abstract is incorporated herein by reference in its entirety.

BACKGROUND

1. Technical Field

The disclosure relates to an inspection device that inspects a state of a workpiece by irradiation, an inspection facility and an inspection device failure confirmation method.

2. Description of Related Art

As this type of inspection device, disclosed is an inspection device that includes a mounting part, a light source part, a photographing part, and an image processing part in a facility in a darkroom (see Japanese Unexamined Patent Application Publication No. 2012-2792 (JP 2012-2792 A)). On the mounting part, a workpiece that is a film is mounted, the light source part irradiates the workpiece, the photographing part photographs the irradiated workpiece and outputs image data, and the image processing part inspects whether or not there is a defect in the workpiece based on the image data. Conventionally, in the inspection device, noise generated when a workpiece is photographed by the photographing part is rejected by the image processing part so as to improve processing efficiency, and, at the same time, enhance accuracy in order to improve a defect detection rate.

SUMMARY

In the inspection device, an open window is provided in a side surface of the darkroom so that a failure of the inspection device is visually confirmed through the open window. A shielding member such as a panel is attached to the open window in order to cover the open window so that light does not enter the inspection device from outside the inspection device during a normal inspection. Meanwhile, when a defect happens in the inspection device, the shielding member is removed in order to confirm the failure of the inspection device through the open window. In this case, since the open window is open, there is a problem that light such as indoor lighting can enter the inspection device from the outside of the inspection device, and affect photographing in the photographing part, thus causing an increase in misdetection.

The disclosure provides an inspection device that is able to block light from entering the inspection device from the outside of the inspection device when the inside of the inspection device is visually inspected. The disclosure also provides an inspection device failure confirmation method.

A first aspect of the disclosure relates to an inspection device that inspects whether or not there is a foreign matter or dirt adhered to a surface of a workpiece or whether or not there is a scratch on the surface of the workpiece. The inspection device includes a mounting part on which the workpiece is mounted, a light source part that irradiates the surface of the workpiece, and a cover part that covers the mounting part and the light source part and blocks light from an outside light source from entering the inspection device, the outside light source being positioned outside the inspection device. A first polarizing plate having a polarizing axis in a first direction is attached to an open window provided in the cover part, and a second polarizing plate having a polarizing axis in a second direction orthogonal to the first direction is attached to the open window so that the second polarizing plate is able to open and close. The second polarizing plate overlaps the first polarizing plate in a state where the second polarizing plate is closed, and the first polarizing plate and the second polarizing plate are present on a straight line that connects the outside light source and the workpiece in a state where the second polarizing plate is open.

In the inspection device, the first polarizing plate having the polarizing axis in the first direction is attached to the open window of the cover part, and the second polarizing plate having the polarizing axis in the second direction orthogonal to the first direction is attached to the open window so that the second polarizing plate is able to open and close. The first polarizing plate has the polarizing axis in the first direction. Light advances while oscillating perpendicularly to the advancing direction. In other words, light advances while making a transverse wave. Therefore, the first polarizing plate only allows transmission of the transverse wave in the first direction along the polarizing axis. Meanwhile, the second polarizing plate has the polarizing axis in the second direction orthogonal to the first direction. The second polarizing plate only allows transmission of a transverse wave in the second direction along the polarizing axis. In other words, the transverse wave in directions other than the second direction is not able to transmit through the second polarizing plate. Therefore, when the first polarizing plate and the second polarizing plate overlap each other so that the polarizing axis in the first direction and the polarizing axis in the second direction become orthogonal to one another, light is not able to transmit through the overlapped first polarizing plate and second polarizing plate.

As a result, in the state where the second polarizing plate is closed, the second polarizing plate overlaps the first polarizing plate so that the polarizing axis in the first direction and the polarizing axis in the second direction become orthogonal to one another. Therefore, light is not able to transmit through the first polarizing plate and the second polarizing plate that overlap each other, and light coming from the outside light source positioned outside the inspection device is blocked from entering the inspection device.

Further, the inspection device is structured so that, in the state where the second polarizing plate is open, the first polarizing plate and the second polarizing plate are present on the straight line that connects the outside light source and the workpiece with each other. The first polarizing plate and the second polarizing plate are provided so that the polarizing axis in the first direction and the polarizing axis in the second direction are orthogonal to each other. With the structure, only a transverse wave of light in the second direction transmits through the second polarizing plate, but the transmitted transverse wave in the second direction is not able to transmit through the first polarizing plate that has the polarizing axis in the first direction orthogonal to the second direction. As a result, even in the state where the second polarizing plate is open, light from the outside light source positioned outside the inspection device is blocked from entering the inspection device.

In the state where the second polarizing plate is open, an angle between the second polarizing plate and the first polarizing plate may be 90 degrees or smaller.

When the angle between the second polarizing plate and the first polarizing plate is 90 degrees or smaller in the state where the second polarizing plate is open, the second polarizing plate and the first polarizing plate block more light trying to enter the inspection device from the outside light source.

The open window of the cover part may be provided in a side surface of the cover part and also at a position lower than the outside light source. The second polarizing plate may be attached so as to be able to open upwardly with respect to the open window.

The open window of the cover part is provided in the side surface of the cover part and also at a position lower than the outside light source, and the second polarizing plate is attached to the open window so that the second polarizing plate is able to open upwardly. Therefore, when the second polarizing plate is open, the second polarizing plate and the first polarizing plate block more light trying to enter the inspection device from the outside light source through the open window.

The inspection device may have a holding device that is configured to hold the second polarizing plate in the open state.

Since the holding device keeps the second polarizing plate open, it is not necessary to support the second polarizing plate in the open state with a hand when a visual inspection of the inside of the inspection device is carried out through the first polarizing plate attached to the open window. Thus, it is possible to carry out an inspection work of the inside of the inspection device easily.

The workpiece may include a fuel cell (a cell of a fuel cell stack).

An outside shape of the fuel cell serving as the workpiece is complex, and irradiation of the fuel cell by the light source part is easily affected by light that is incident from the outside light source. Since the second polarizing plate and the first polarizing plate block light trying to enter the inspection device from the outside light source, the inspection of the fuel cell is not affected by light entering the inspection device from the outside light source, and is thus carried out highly accurately.

A second aspect of the disclosure relates to an inspection facility that inspects whether or not there is a foreign matter or dirt adhered to a surface of a workpiece or whether or not there is a scratch on the surface of the workpiece, the inspection facility including the inspection device and the outside light source.

A third aspect of the disclosure relates to an inspection device failure confirmation method in which a failure of an inspection device is confirmed, the inspection device detecting whether or not there is a foreign matter or dirt adhered to a surface of a workpiece or whether or not there is a scratch on the surface of the workpiece. The inspection device includes a mounting part on which the workpiece is mounted, a light source part that irradiates a surface of the workpiece, and a cover part that covers the mounting part and the light source part and blocks light coming from an outside light source from entering the inspection device, the outside light source being positioned outside the inspection device. The first polarizing plate having a polarizing axis in a first direction is attached to an open window provided in the cover part, and a second polarizing plate having a polarizing axis in a second direction orthogonal to the first direction is attached to the open window so that the second polarizing plate is able to open and close. The outside light source and the inspection device are arranged so that the second polarizing plate overlaps the first polarizing plate in a state where the second polarizing plate is closed, and the first polarizing plate and the second polarizing plate are present on a straight line that connects the outside light source and the workpiece in the state where the second polarizing plate is open. The inside of the inspection device is visually inspected through the first polarizing plate in the state where second polarizing plate is open so that it is able to confirm whether or not there is a failure in the inspection device.

The inspection device that is confirmed by using the inspection device failure confirmation method is structured similarly to the inspection device according to the first aspect of the disclosure. Therefore, whether the second polarizing plate is closed or open, light from the outside light source positioned outside the inspection device is blocked from entering the inspection device. As a result, it is possible to carry out a visual inspection of the inside of the inspection device through the first polarizing plate having the polarizing axis in the first direction in the state where the second polarizing plate is open and light from the outside light source is blocked from entering the inspection device. With the visual inspection, it is possible to confirm a failure of the inspection device without being affected by light from the outside light source.

In the state where the second polarizing plate is open, an angle between the second polarizing plate and the first polarizing plate may be 90 degrees or smaller When the angle between the second polarizing plate and the first polarizing plate is 90 degrees or smaller in the state where the second polarizing plate is open, the second polarizing plate and the first polarizing plate block more light that tries to enter the inspection device from the outside light source, and, in this state, a visual inspection of the inside of the inspection device is carried out through the first polarizing plate. With the visual inspection, it is possible to confirm a failure of the inspection device without being affected by light from the outside light source.

The workpiece may include a fuel cell.

An outside shape of the fuel cell serving as the workpiece is complex, and irradiation of the fuel cell by the light source part is easily affected by light that is incident from the outside light source. Since the second polarizing plate and the first polarizing plate block light trying to enter the inspection device from the outside light source, failure confirmation of the fuel cell in the inspection device is not affected by light entering the inspection device from the outside light source, and is thus carried out highly accurately.

According to the disclosure, it is possible to provide the inspection device that is able to block entry of light into the inspection device from outside of the inspection device when a visual inspection of the inside of the inspection device is carried out. Also, the inspection device failure confirmation method is provided.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

An inspection device 100 and an inspection device failure confirmation method according to an embodiment are described with reference to the drawings. An inspection device and an inspection device failure confirmation method according to the disclosure are applied to the embodiment.

Figure 1:
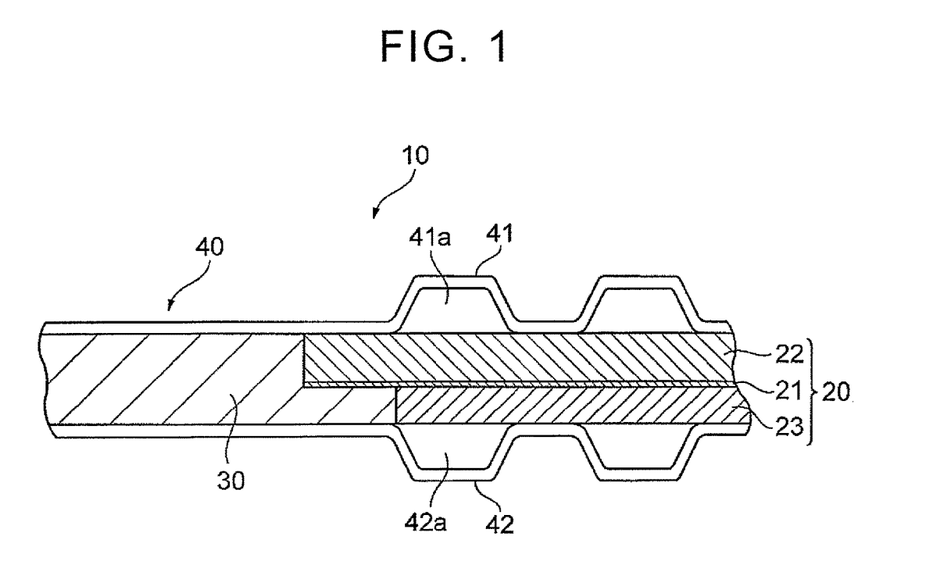
FIG. 1 is partial sectional view of a fuel cell to be inspected by an inspection device according to an embodiment of the disclosure.

A workpiece inspected by the inspection device 100 according to the embodiment is not particularly limited as an inspection object, but may be made of, for example, a fuel cell 10 (a cell of a fuel cell stack). As shown in FIG. 1, the fuel cell 10 includes a membrane electrode and gas diffusion layer assembly (hereinafter referred to as an MEGA) 20, a seal member 30, and a separator 40.

The MEGA 20 includes a membrane electrode assembly (hereinafter referred to as an MEA) 21, an anode-side gas diffusion layer (hereinafter referred to as a GDL) 22, and a cathode-side GDL 23.

The MEA 21 is made of an assembly of an electrolyte membrane (not shown), an anode catalyst layer, and a cathode catalyst layer. The electrolyte membrane is formed by using a polymer electrolyte resin that is a solid polymeric material such as perfluorosulfonic acid (PFSA) ionomer, and is made of an ion exchange membrane in which an ion-conductive polymer membrane serves as an electrolyte. The electrolyte membrane has functions of obstructing flows of electrons and gas and allowing protons to move from the anode catalyst layer to the cathode catalyst layer.

The anode catalyst layer is an electrode catalyst layer that is formed by coating a carbon particle with proton-conductive ionomer. The carbon particle is, for example, a catalyst-carrying carbon particle that is made of a conductive carrier carrying a catalyst such as platinum, a platinum alloy, and so on. The anode catalyst layer has a function of breaking down hydrogen gas ($H_2$) into protons and electrons. Although the cathode catalyst layer is made from materials similar to those of the anode catalyst layer, the cathode catalyst layer has a function of generating water out of protons, electrons, and oxygen, unlike the anode catalyst layer.

The anode-side GDL 22 is made from a material having gas permeability and conductivity, that is, for example, a porous fiber base material such as carbon paper in which carbon fiber, graphite fiber, or the like is used. The anode-side GDL 22 is joined to an outer side of the anode catalyst layer, and has a function of diffusing hydrogen gas serving as fuel gas so that hydrogen gas is made uniform and spreads across the anode catalyst layer.

Similarly to the anode-side GDL 22, the cathode-side GDL 23 is made from a material having gas permeability and conductivity, that is, for example, a porous fiber base material such as carbon paper in which carbon fiber, graphite fiber, or the like is used. The cathode-side GDL 23 is joined to an outer side of the cathode catalyst layer, and has a function of diffusing air ($O_2$) serving as oxidant gas so that air is made uniform and spreads across the cathode catalyst layer.

The seal member 30 is made from synthetic resin and formed into a frame shape. The MEGA 20 is joined to the seal member 30. The seal member 30 has a function of preventing so-called cross leakage and electrical short circuit between catalytic electrodes. Cross leakage means that small amounts of hydrogen ($H_2$) of a fuel electrode and oxygen ($O_2$) of an air electrode pass through the electrolyte membrane.

The separator 40 includes an anode-side separator 41 and a cathode-side separator 42. The anode-side separator 41 is joined to the anode-side GDL 22 of the MEGA 20, and a fuel gas flow passage 41a is formed along a surface of the anode-side GDL 22. In fuel gas flow passage 41a, hydrogen serving as fuel gas is allowed to flow. The cathode-side separator 42 is joined to the cathode-side GDL 23 of the MEGA 20, and an oxidant gas flow passage 42a is formed along a surface of the cathode-side GDL 23. In the oxidant gas flow passage 42a, air serving as oxidant gas is allowed to flow.

Next, a manufacturing method for the fuel cell 10 including the inspection device 100 and the inspection device failure confirmation method according to the embodiment is described with reference to the drawings.

Figure 2:
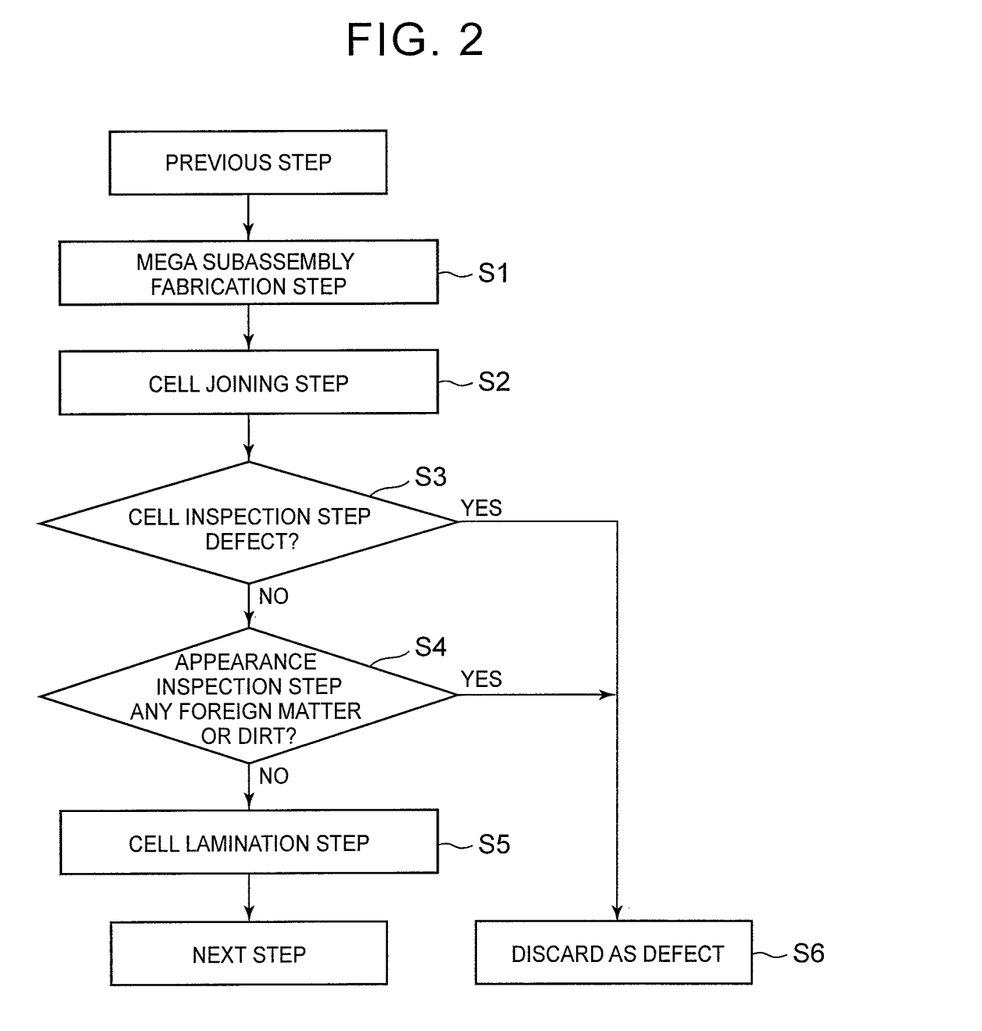
FIG. 2 is a process flow showing a manufacturing process for the fuel cell to be inspected by the inspection device according to the embodiment of the disclosure.

As shown in FIG. 2, the manufacturing method for the fuel cell 10 according to the embodiment includes an MEGA subassembly fabrication step, a cell joining step, a cell inspection step, an appearance inspection step, and a cell lamination step. These steps are carried out in order.

In the MEGA subassembly fabrication step, the anode-side GDL 22 and the cathode-side GDL 23 are joined to the MEA 21 transferred from a previous step, and the MEGA 20 is thus fabricated. Next, the seal member 30 is joined to the fabricated MEGA 20, and an adhesive sheet is assembled to the seal member 30. Thus, an MEGA subassembly is fabricated (step S1).

In the cell joining step, the MEGA subassembly transferred from the MEGA subassembly fabrication step and the separator 40 fabricated in a different step (not shown) are assembled, and the fuel cell 10 is thus fabricated (step S2). The separator 40 is made of the anode-side separator 41 and the cathode-side separator 42. The anode-side separator 41 is joined to the anode-side GDL 22 of the MEGA subassembly, and the cathode-side separator 42 is joined to the cathode-side GDL 23 in the MEGA subassembly.

Figure 3:
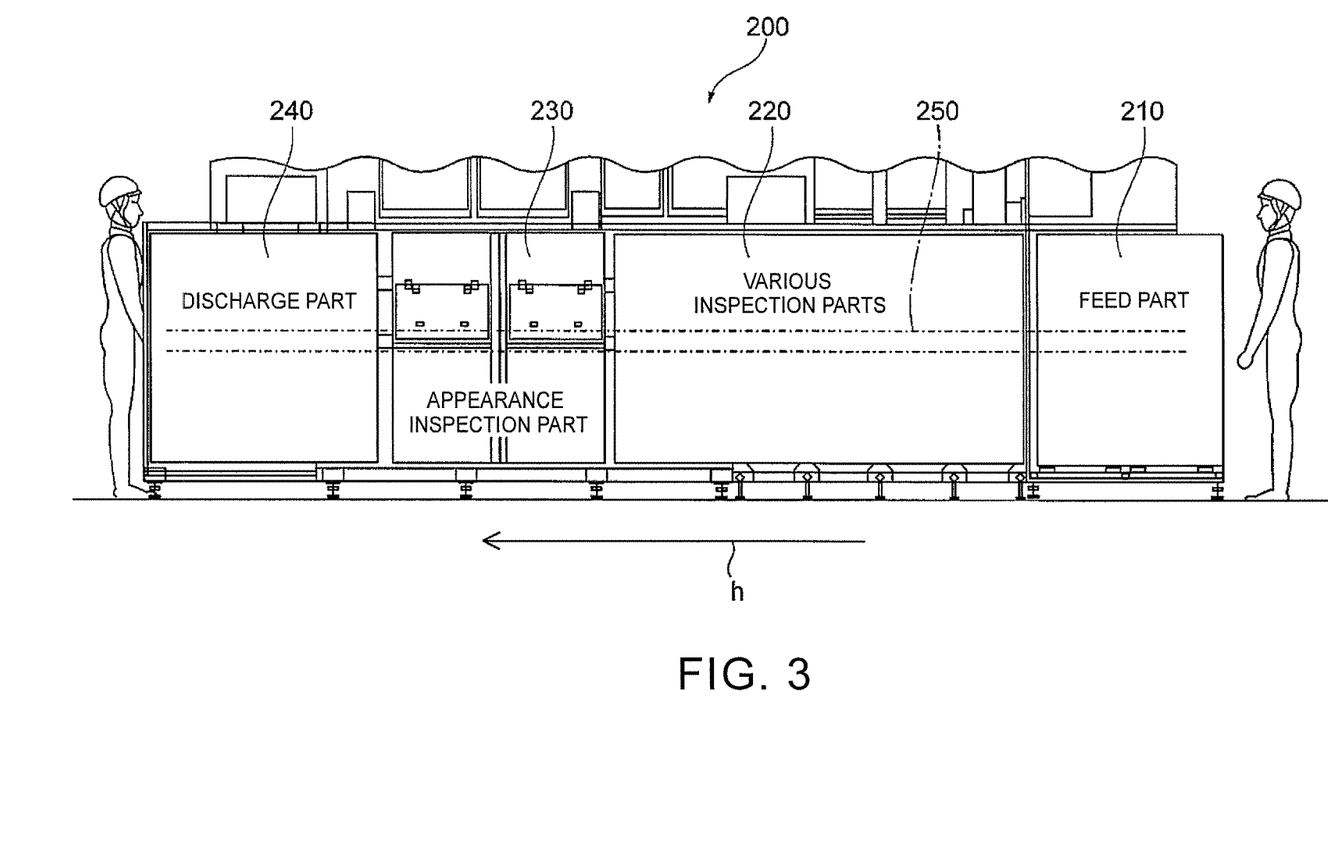
FIG. 3 is a side view of an inspection facility including the inspection device according to the embodiment of the disclosure.

As shown in FIG. 3, in the cell inspection step, the fuel cell 10 fabricated in the cell joining step is inspected in an inspection facility 200. The inspection facility 200 includes a feed part 210, various inspection parts 220, an appearance inspection part 230, a discharge part 240, and a transfer part 250. In the inspection facility 200, the fuel cell 10 fed from the feed part 210 is transferred by the transfer part 250 in a transfer direction shown by an arrow h, and discharged from the discharge part 240 after going through the various inspection parts 220 and the appearance inspection part 230.

In the cell inspection step, various inspections other than appearance inspection that is carried out later in the appearance inspection step are carried out for the fuel cell in the various inspection parts 220 (step S3). The fuel cell 10 determined as a defect in the cell inspection step is discarded as a defect (step S6). The fuel cell 10 that is not determined as a defect in the cell inspection step is transferred to the appearance inspection step.

In the appearance inspection step, the fuel cell 10 transferred by the transfer part 250 is inspected in the appearance inspection part 230 of the inspection facility 200 to determine whether or not there is abnormality in an appearance of the fuel cell 10 such as adhesion of a foreign matter or dirt, and a scratch (step S4). The inspection device 100 that structures the appearance inspection part 230 carries out the appearance inspection step.

As shown in FIG. 4A, FIG. 4B, FIG. 5A, and FIG. 5B, the inspection device 100 includes a mounting part, the light source part 110, a cover part 120, a pair of polarization parts 130, a detection part 140, and a control part (not shown). The mounting part structures the transfer part 250 of the inspection facility 200, and the fuel cell 10 is mounted on the mounting part.

The fuel cell 10 is mounted on the mounting part that serves as the transfer part 250, and the mounting part transfers the fuel cell 10 at given transfer speed (m/second) in the transfer direction shown by the arrow h. The light source part 110 is made of a plurality of light sources that are provided inside the inspection device 100 corresponding to a complex outer shape of the fuel cell 10, and irradiates the fuel cell 10 with light coming from each of the light sources.

The cover part 120 is made of a wall member that entirely covers the transferred fuel cell 10, the mounting part, and the light source part 110, and blocks light from an outside light source 300 positioned outside the inspection device 100 so that the light does not enter the inspection device 100. Therefore, the inside of the inspection device 100 covered by the cover part 120 becomes a darkroom. A pair of rectangular open windows 120a is provided in the wall member of the cover part 120 on one side. The open windows 120a go through the wall member and separated from one another in the transfer direction. Through each of the open windows 120a, one is able to see the inside of the inspection device 100 from the outside of the inspection device 100.

Figure 4A:
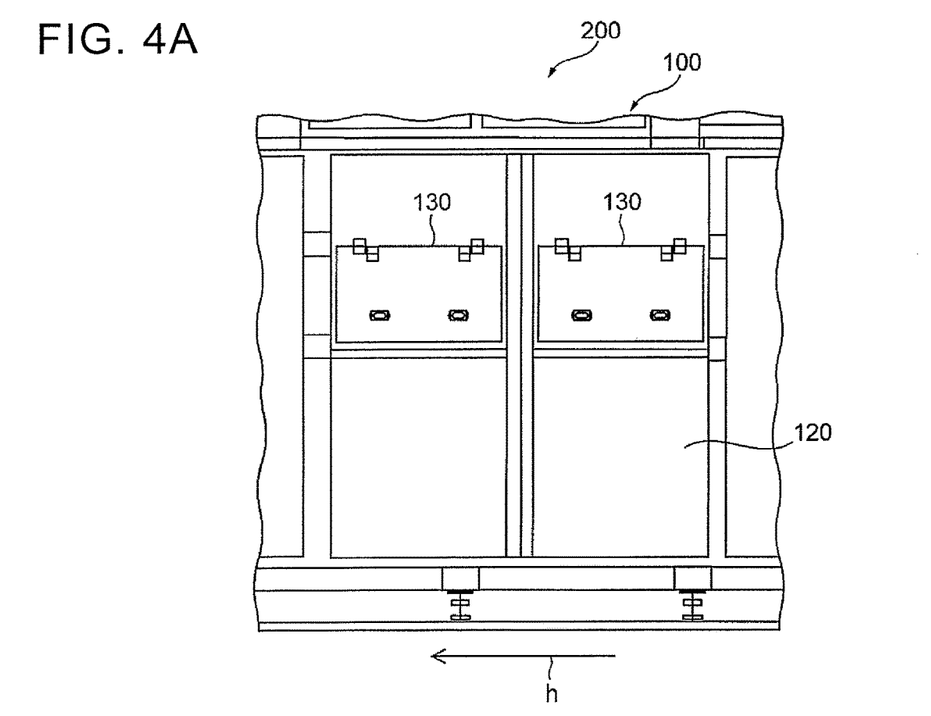
FIG. 4A is a side view of the inspection device according to the embodiment of the disclosure, showing a part of the inspection device.

The open windows 120a are provided on a side surface of the cover part 120 at positions lower than the outside light source 300. When the inspection device 100 is installed on a floor surface of a building, a lighting fixture attached to a ceiling of the building serves as the outside light source 300, and light from the lighting fixture hits the open windows 120a from above.

Figures 5A, 5B:
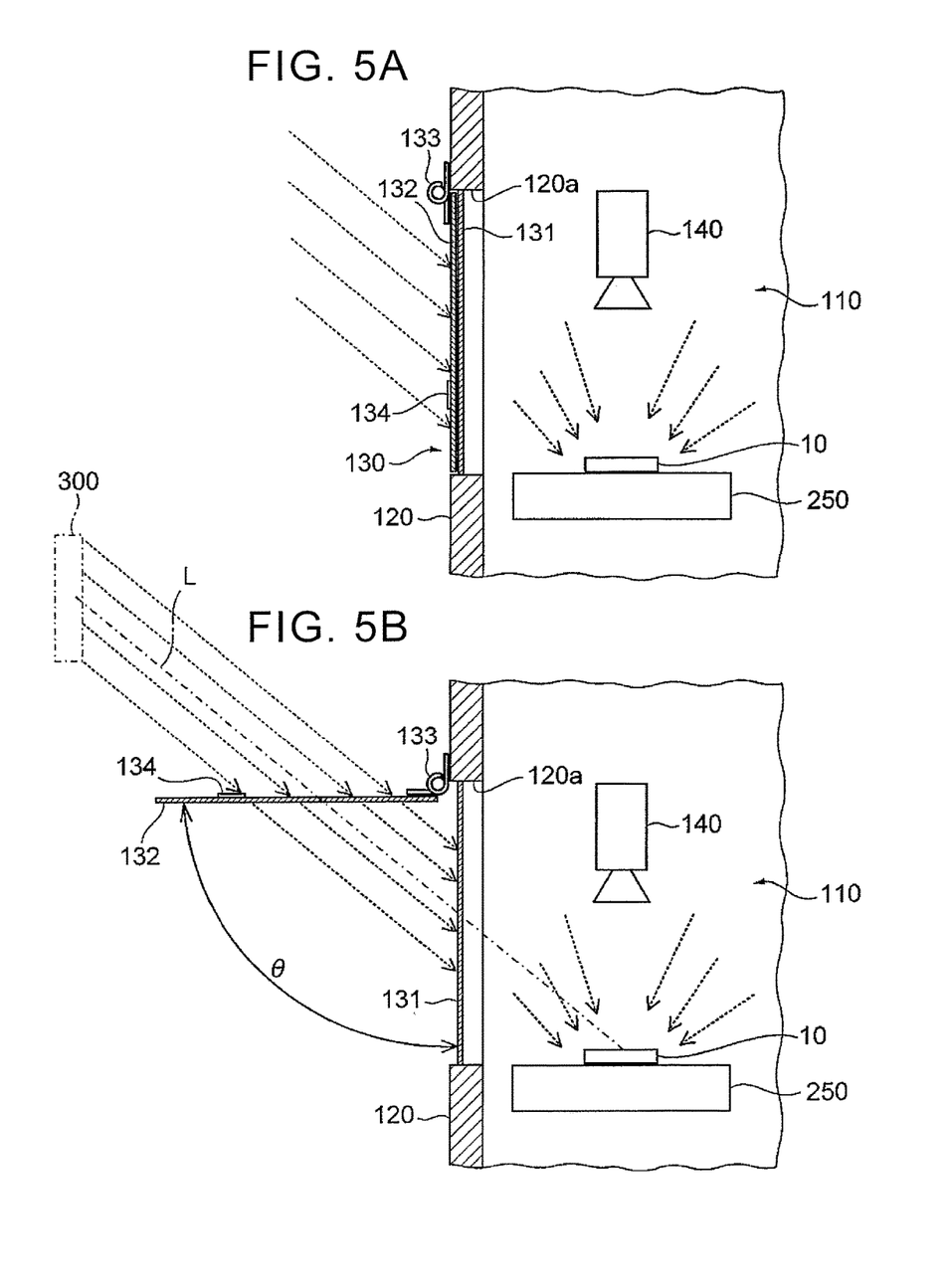
FIG. 5A is a partial sectional view in which the inspection device according to the embodiment of the disclosure is cut off in a state where a second polarizing plate is closed.
FIG. 5B is a partial sectional view in which the inspection device according to the embodiment of the disclosure is cut off in a state where the second polarizing plate is open.

As shown in FIG. 4A, the polarization parts 130 are attached to the open windows 120a of the cover part 120, respectively. As shown in FIG. 5A and FIG. 5B, each of the polarization parts 130 is made of a first polarizing plate 131, a second polarizing plate 132, a pair of hinges 133, and a pair of handgrips 134.

The first polarizing plate 131 is made of a transparent member, and has a polarizing axis p1 in a first direction. Light advances while oscillating perpendicularly to the advancing direction. In other words, light advances while making a transverse wave. Therefore, the first polarizing plate 131 allows transmission of the transverse wave in the first direction along the polarizing axis p1 only. Here, the first direction means a direction perpendicular to the transfer direction shown by the arrow h in FIG. 4A. As shown in FIG. 5A and FIG. 5B, the first polarizing plate 131 is tightly fitted into the open window 120a and fixed.

Similarly to the first polarizing plate 131, the second polarizing plate 132 is made of a transparent member, and has a polarizing axis p2 in a second direction orthogonal to the first direction. The second polarizing plate 132 allows transmission of a transverse wave of light in the second direction along the polarizing axis p2 only. The second direction means the transfer direction shown by the arrow h in FIG. 4A. As shown in FIG. 5A and FIG. 5B, the second polarizing plate 132 is attached to the cover part 120 in the vicinity of the open window 120a by the hinges 133 so that the second polarizing plate 132 is able to open and close.

The second polarizing plate 132 is attached so as to be able to open upwardly with respect to the open window 120a. One end of the second polarizing plate 132 is pivotally supported by the hinges 133 in the side surface of the cover part 120 and also in the vicinity of an upper end of the open window 120a, and the second polarizing plate 132 is open as the other end of the second polarizing plate 132 is lifted in the upward direction that is a direction away from the side surface of the cover part 120. A holding device is provided between the second polarizing plate 132 and the cover part 120. The holding device is structured so as to be able to hold the second polarizing plate 132 in an open state, and the second polarizing plate 132 is thus able to stand still at an arbitrary angle θ.

In the description above, the first direction of the polarizing axis p1 of the first polarizing plate 131 is referred to as a direction perpendicular to the transfer direction shown by the arrow h in FIG. 4A, and the second direction of the polarizing axis p2 of the second polarizing plate 132 is referred to as the transfer direction shown by the arrow h in FIG. 4A. However, the first direction and the second direction may be other directions as long as they are orthogonal to each other. For example, the polarizing axis p1 of the first polarizing plate 131 may be in the second direction, and the polarizing axis p2 of the second polarizing plate 132 may be in the first direction.

Figure 4B:
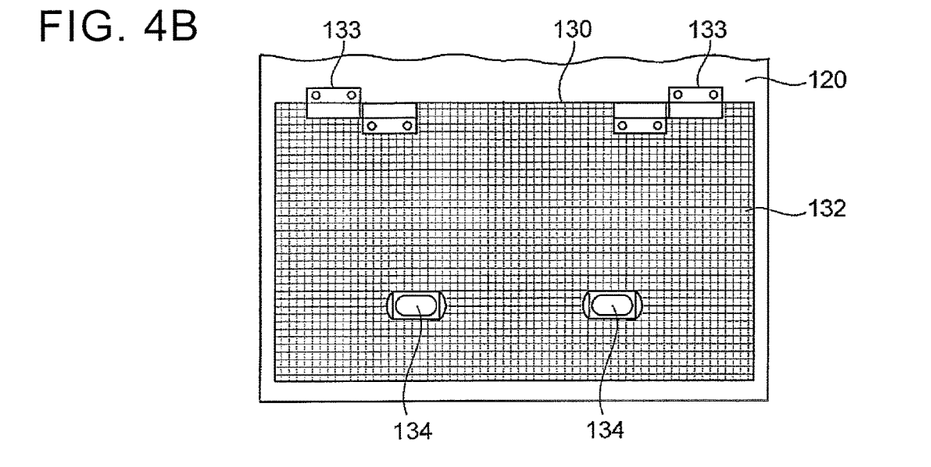
FIG. 4B is a side view of the inspection device according to the embodiment of the disclosure, and is an enlarged side view of a part of the inspection device.
Figure 6:
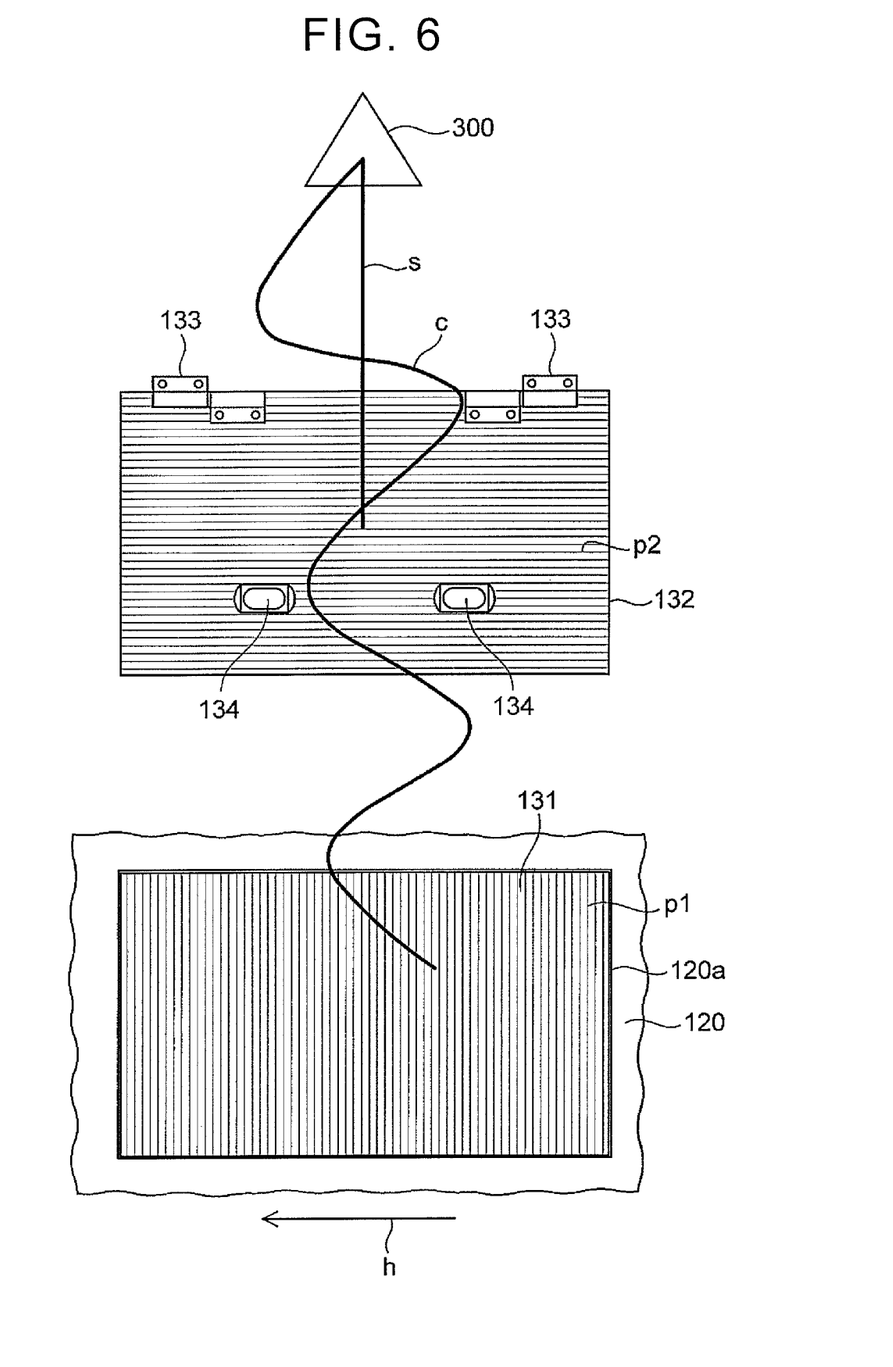
FIG. 6 is a view describing transmission of light through the second polarizing plate and a first polarizing plate of the inspection device according to the embodiment of the disclosure.

When the second polarizing plate 132 overlap the first polarizing plate 131 as shown in FIG. 4B and FIG. 5A, in other words, when the second polarizing plate 132 is closed, the polarizing axis p2 in the second direction and the polarizing axis p1 in the first direction become orthogonal to one another. In this case, as shown in FIG. 6, the direction of the transverse wave of light shown by a curve c coincides with the second direction of the polarizing axis p2 of the second polarizing plate 132. Therefore, the transverse wave of light shown by the curve c transmits through the second polarizing plate 132 and reaches the first polarizing plate 131.

However, the direction of the transverse wave of light shown by the curve c does not coincide with the first direction of the polarizing axis p1 of the first polarizing plate 131. This means that the direction of the transverse wave of light shown by the curve c is orthogonal to the first direction of the polarizing axis p1 of the first polarizing plate 131. Therefore, the transverse wave of light shown by the curve c is not able to transmit through the first polarizing plate 131, and is blocked by the first polarizing plate 131. As a result, in the state shown in FIG. 5A where the second polarizing plate 132 is closed, light from the outside light source 300 of the inspection device 100 is blocked by the second polarizing plate 132 and the first polarizing plate 131, and is not able to enter the inspection device 100.

The transverse wave of light shown by a straight line S in FIG. 6 does not coincide with the second direction of the polarizing axis p2 of the second polarizing plate 132. Therefore, the transverse wave of light is not able to transmit through the second polarizing plate 132, and is blocked by the second polarizing plate 132.

The inspection device 100 is structured so that, in the state where the second polarizing plate 132 is open as shown in FIG. 5B, the first polarizing plate 131 and the second polarizing plate 132 are present on a straight line L that connects a center portion of the outside light source 300 of the inspection device 100 and a center portion of the fuel cell 10 serving as a workpiece. With the structure, similarly to the state where the second polarizing plate 132 is closed, when the second polarizing plate 132 is open, light traveling from the outside light source 300 towards the inside of the inspection device 100 is able to transmit through the second polarizing plate 132, but is blocked by the first polarizing plate 131 and is thus not able to enter the inspection device 100.

Hence, when the second polarizing plate 132 is open, it is preferred that an angle θ between the second polarizing plate 132 and the first polarizing plate 131 shown in FIG. 5B, in other words, an opening-closing angle θ be an angle that makes it possible to block as much light from the outside light source 300 as possible. On the other hand, when an operator visually inspects the inside of the inspection device 100 from the first polarizing plate 131 in the state where the second polarizing plate 132 is open, it is preferred that the second polarizing plate 132 is open at the largest possible angle so as not to obstruct the operation. Specifically, it is preferred that the angle θ is in a range from about 80 degrees to 100 degrees, and an angle of 90 degrees is the most preferred.

As shown in FIG. 4A and FIG. 4B, the handgrips 134 are attached to the second polarizing plate 132 so as to be separated from each other along the transfer direction shown by the arrow h. When an operator opens or closes the second polarizing plate 132, the operator grips the handgrips 134.

The detection part 140 is made of a device that detects appearance of the fuel cell 10 and captures it as an image. The detection part 140 includes, for example, an image pickup device such as a charge-coupled device (CCD) image sensor and a complementary metal-oxide-semiconductor (CMOS) image sensor. An image captured by the detection part 140 is transmitted to the control part. Based on the transmitted image, the control part detects whether or not a foreign matter or dirt is adhered to the fuel cell 10, or the fuel cell 10 is scratched, and determines whether or not the fuel cell 10 is a defect.

In the cell lamination step, a stack is formed by laminating a plurality of the fuel cells 10, and the laminated fuel cells 10 are electrically connected with each other. Conductive collector plates are arranged on outer sides of both ends of the stack in a lamination direction of the fuel cells 10, respectively, and the collector plates are electrically connected with the stack. A pair of endplates is arranged on outer sides of the collector plates, respectively. The endplates sandwich the stack and are insulated from the collector plates. The endplates are fastened by side plates, respectively, and the endplates thus cover a periphery of the stack so that the stack is held (step S5). The stack in which the fuel cells 10 are laminated is transferred to the next step.

Next, the inspection device failure confirmation method according to the embodiment is described with reference to the drawings.

The inspection device failure confirmation method according to the embodiment is made of a method of confirming whether or not the inspection device 100 has a failure. As shown in FIG. 5B, this method is structured so that a failure of the inspection device 100 is confirmed as the inside of the inspection device 100 is visually inspected through the first polarizing plate 131 in the state where the second polarizing plate 132 of the polarization part 130 of the inspection device 100 is open.

In the inspection device failure confirmation method according to the embodiment, as described earlier, light from the outside light source 300 is blocked by the second polarizing plate 132 and the first polarizing plate 131 from entering the inspection device 100 even when the second polarizing plate 132 is open. Therefore, it is possible to confirm a failure of the inspection device 100 through the transparent first polarizing plate 131 without being affected by light form the outside light source 300.

Effects of the inspection device 100 and the inspection device failure confirmation method structured as above according to the embodiment are described.

In the inspection device 100 according to the embodiment, the first polarizing plate 131 having the polarizing axis p1 in the first direction is attached to each of the open windows 120a on the side surface of the cover part 120. Also, the second polarizing plate 132 having the polarizing axis p2 in the second direction orthogonal to the first direction is attached to each of the open windows 120a. With this structure, the polarizing axis p1 of the first polarizing plate 131 is in the first direction, and light advances in the transverse wave that is perpendicular to the advancing direction. Therefore, only the transverse wave in the first direction along the polarizing axis p1 transmits through the first polarizing plate 131.

Meanwhile, the polarizing axis p2 of the second polarizing plate 132 is in the second direction orthogonal to the first direction, and only the transverse wave in the second direction along the polarizing axis p2 transmits through the second polarizing plate 132. In other words, the transverse wave in directions other than the second direction is not able to transmit through the second polarizing plate 132. Therefore, when the first polarizing plate 131 and the second polarizing plate 132 overlap each other so that the polarizing axis p1 in the first direction and the polarizing axis p2 in the second direction become orthogonal to one another, light is not able to transmit through the first polarizing plate 131 and the second polarizing plate 132 that overlap each other.

With the structure, in the state where the second polarizing plate 132 is closed, the second polarizing plate 132 overlaps the first polarizing plate 131 so that the polarizing axis p1 in the first direction and the polarizing axis p2 in the second direction become orthogonal to one another. Therefore, light is not able to transmit through the first polarizing plate 131 and the second polarizing plate 132 that overlap each other, and light from the outside light source 300 that is positioned outside the inspection device 100 is blocked from entering the inspection device 100.

As a result, with the inspection device 100 according to the embodiment, an effect is obtained that light from the outside light source 300 is blocked from entering the inspection device 100 in the state where the second polarizing plate 132 is closed, and the darkroom inside the inspection device 100 is not affected by the outside light source 300.

Further, the inspection device 100 according to the embodiment is structured so that the first polarizing plate 131 and the second polarizing plate 132 are present on the straight line L that connects the outside light source 300 and the fuel cell 10 in the state where the second polarizing plate 132 is open. Even when the second polarizing plate 132 is open, the first polarizing plate 131 and the second polarizing plate 132 maintain a relation that the polarizing axis p1 in the first direction and the polarizing axis p2 in the second direction are orthogonal to each other.

With the structure, only the transverse wave, c of light in the second direction transmits through the second polarizing plate 132, but the transmitted transverse wave c in the second direction is not able to transmit through the first polarizing plate 131 that has the polarizing axis p1 in the first direction orthogonal to the second direction. As a result, even in the state where the second polarizing plate 132 is open, light from the outside light source 300 that is positioned outside the inspection device 100 is blocked from entering the inspection device 100. Hence, even in the state where the second polarizing plate 132 is open, the darkroom inside the inspection device 100 is not affected by light from the outside light source 300. Therefore, an effect is obtained that misdetection by the detection part 140 is prevented, and the fuel cell 10 having a complex outside shape is inspected highly accurately.

Further, the inspection device 100 according to the embodiment is structured so that, in the state where the second polarizing plate 132 is open, an angle between the second polarizing plate 132 and the first polarizing plate 131 becomes 90 degrees or smaller, and entrance of light from the outside light source 300 is blocked as much as possible. With the structure, the second polarizing plate 132 and the first polarizing plate 131 block as much light as possible that tries to enter the inspection device 100 from the outside light source 300. As a result, an effect is obtained that there is no influence imposed by light coming from the outside light source 300, misdetection by the detection part 140 is thus prevented, and the fuel cell 10 having the complex outside shape is inspected highly accurately.

Furthermore, in the inspection device 100 according to the embodiment, the second polarizing plate 132 is attached to the cover part 120 in a movable manner, in other words, the second polarizing plate 132 is attached to the cover part 120 through the hinges 133 so that the second polarizing plate 132 is able to open and close. Therefore, it is possible to repeat the inspection in the same conditions. Thus, an effect is obtained that while maintaining illuminance for operations carried out outside the facility, inspection conditions are stabilized for both normal inspection and inspection at the time of a defect, in other words, for both steady and non-steady time. Therefore, it is possible to maintain quality and operations.

Further, in the inspection device 100 according to the embodiment, the open windows 120a of the cover part 120 are provided in the side surface of the cover part 120 and also at positions lower than the outside light source 300. The second polarizing plate 132 is attached so as to be able to open upwardly with respect to each of the open windows 120a. Therefore, in the state where the second polarizing plate 132 is open upwardly, the second polarizing plate 132 and the first polarizing plate 131 block as much light as possible that tries to enter the inspection device 100 from the outside light source 300 through the open window 120a.

The inspection device failure confirmation method according to the embodiment is structured so that, when a failure of the inspection device 100 according to the embodiment is confirmed, an operator visually inspects the inside of the inspection device 100 through the first polarizing plate 131 in the state where the second polarizing plate 132 is open. With the structure, when the operator confirms a defect inside the inspection device 100 from the outside of the inspection device 100, light from the outside light source 300 is kept blocked from entering the inspection device 100 even in the state where the second polarizing plate 132 is open. In this state, the operator is able to visually inspect the inside of the inspection device 100 through the transparent first polarizing plate 131 having the polarizing axis p1 in the first direction. Thus, an effect is obtained that, with the visual inspection, a failure of the inspection device is confirmed without being affected by light from the outside light source 300.

In related arts, when a failure of the inside of an inspection device is confirmed, a detachable panel provided in a wall surface of the inspection device is removed, and a visual inspection of the inside is carried out through an opening portion to confirm the failure. With this method, light from an outside light source enters the inspection device from the opening portion at the time of the visual inspection. This causes a problem that misdetection increases, making it difficult to maintain quality of fuel cells and operation of the device. On the contrary, with the inspection device failure confirmation method according to the embodiment, there is an effect that light from the outside light source does not enter the inspection device, and the problem of the related arts is solved.

Further, the inspection device 100 according to the embodiment is provided with the holding device that is structured so as to hold the second polarizing plate 132 in the opened state. Therefore, when a visual inspection of the inside of the inspection device 100 is carried out through the first polarizing plate 131 attached to each of the open windows 120a, an operator does not need to support the second polarizing plate 132 in the open state, and it is thus possible to carry out inspection work for the inside of the inspection device 100 easily.

Further, in the inspection device failure confirmation method according to the embodiment, the angle between the second polarizing plate 132 and the first polarizing plate 131 is 90 degrees or smaller in the state where the second polarizing plate 132 is open, so that entrance of light from the outside light source 300 is blocked as much as possible. With the structure, the second polarizing plate 132 and the first polarizing plate 131 block as much light as possible that tries to enter the inspection device 100 from the outside light source 300. As a result, the inside of the inspection device 100 is visually inspected through the first polarizing plate 131 without being affected by light from the outside light source 300. Thus, an effect is obtained that the visual inspection makes it possible to confirm a failure of the inspection device without being affected by light from the outside light source 300.

The embodiment according to the disclosure has been described in detail. However, the disclosure is not limited to the embodiment, and various design changes may be made.

What is claimed is:

1. An inspection device that inspects whether or not there is a foreign matter or dirt adhered to a surface of a workpiece or whether or not there is a scratch on the surface of the workpiece, the inspection device comprising:
   a mounting part on which the workpiece is mounted;
   a light source part that irradiates the surface of the workpiece; and
   a cover part that covers the mounting part and the light source part and blocks light coming from an outside light source from entering the inspection device, the outside light source being positioned outside the inspection device, wherein:

a first polarizing plate having a polarizing axis in a first direction is attached to an open window provided in the cover part, and a second polarizing plate having a polarizing axis in a second direction orthogonal to the first direction is attached to the open window so that the second polarizing plate is able to open and close; and the second polarizing plate overlaps the first polarizing plate in a state where the second polarizing plate is closed, and the first polarizing plate and the second polarizing plate are present on a straight line that connects the outside light source and the workpiece in a state where the second polarizing plate is open.

2. The inspection device according to claim 1, wherein an angle between the second polarizing plate and the first polarizing plate is 90 degrees or smaller in the state where the second polarizing plate is open.

3. The inspection device according to claim 1, wherein:
the open window of the cover part is provided in a side surface of the cover part and at a position lower than the outside light source; and
the second polarizing plate is attached so as to be able to open upwardly with respect to the open window.

4. The inspection device according to claim 3, further comprising a holding device that is configured to hold the second polarizing plate in the state where the second polarizing plate is open.

5. The inspection device according to claim 1, wherein the workpiece includes a fuel cell.

6. An inspection facility that detects whether or not there is a foreign matter or dirt adhered to a surface of a workpiece or whether or not there is a scratch on the surface of the workpiece, the inspection facility comprising:
the inspection device according to claim 1; and
the outside light source.

7. An inspection device failure confirmation method in which a failure of an inspection device is confirmed, the inspection device detecting whether or not there is a foreign matter or dirt adhered to a surface of a workpiece or whether or not there is a scratch on the surface of the workpiece, wherein:
the inspection device includes a mounting part on which the workpiece is mounted, a light source part that irradiates the surface of the workpiece, and a cover part that covers the mounting part and the light source part and blocks light coming from an outside light source from entering the inspection device, the outside light source being positioned outside the inspection device;
a first polarizing plate having a polarizing axis in a first direction is attached to an open window provided in the cover part, and a second polarizing plate having a polarizing axis in a second direction orthogonal to the first direction is attached to the open window so as to be able to open and close;
the inspection device failure confirmation method, comprising:
installing the outside light source and the inspection device so that the second polarizing plate overlaps the first polarizing plate in a state where the second polarizing plate is closed, and the first polarizing plate and the second polarizing plate are present on a straight line that connects the outside light source and the workpiece in the state where the second polarizing plate is open; and
inspecting an inside of the inspection device visually through the first polarizing plate in the state where the second polarizing plate is open so that it is able to confirm whether or not there is a failure in the inspection device.

8. The inspection device failure confirmation method according to claim 7, wherein an angle between the second polarizing plate and the first polarizing plate is 90 degrees or smaller in the state where the second polarizing plate is open.

9. The inspection device failure confirmation method according to claim 7, wherein the workpiece includes a fuel cell.

* * * * *